(12) United States Patent
Nolte

(10) Patent No.: US 7,843,844 B2
(45) Date of Patent: Nov. 30, 2010

(54) METHOD, APPARATUS AND SYSTEM FOR THE ADAPTIVE OPTIMIZATION OF TRANSPORT PROTOCOLS WHEN TRANSMITTING IMAGES

(75) Inventor: Bjoern Nolte, Fürth (SE)

(73) Assignee: Siemens Aktiengesellschaft, Munich (DE)

( * ) Notice: Subject to any disclaimer, the term of this patent is extended or adjusted under 35 U.S.C. 154(b) by 1525 days.

(21) Appl. No.: 11/189,880

(22) Filed: Jul. 27, 2005

(65) Prior Publication Data
US 2006/0023631 A1 Feb. 2, 2006

(30) Foreign Application Priority Data
Jul. 28, 2004 (DE) .................. 10 2004 036 488

(51) Int. Cl.
*H04J 3/14* (2006.01)
*H04J 3/22* (2006.01)
*H04L 12/56* (2006.01)
*G06F 15/16* (2006.01)

(52) U.S. Cl. .................. 370/252; 370/466; 370/395.6; 709/232

(58) Field of Classification Search .............. 370/252, 370/395.6, 254, 401, 465, 466; 709/232
See application file for complete search history.

(56) References Cited

U.S. PATENT DOCUMENTS

| | | | | |
|---|---|---|---|---|
| 5,491,693 A | * | 2/1996 | Britton et al. ............... 370/401 |
| 6,016,307 A | * | 1/2000 | Kaplan et al. ............... 370/238 |
| 6,088,356 A | * | 7/2000 | Hendel et al. ............... 370/392 |
| 6,091,733 A | * | 7/2000 | Takagi et al. ............... 370/401 |
| 6,137,527 A | | 10/2000 | Abdel-Malek et al. |
| 6,144,641 A | * | 11/2000 | Kaplan et al. ............... 370/238 |
| 6,289,115 B1 | * | 9/2001 | Takeo ......................... 382/130 |
| 6,456,594 B1 | * | 9/2002 | Kaplan et al. ............... 370/238 |
| 6,473,404 B1 | * | 10/2002 | Kaplan et al. ............... 370/238 |
| 6,598,011 B1 | * | 7/2003 | Howards Koritzinsky et al. 702/185 |
| 6,976,080 B1 | * | 12/2005 | Krishnaswamy et al. .... 709/230 |
| 7,307,956 B2 | * | 12/2007 | Kaplan et al. ............... 370/238 |
| 7,426,567 B2 | * | 9/2008 | Wortmann et al. .......... 709/231 |
| 2002/0141353 A1 | * | 10/2002 | Ludwig et al. .............. 370/254 |
| 2004/0028071 A1 | | 2/2004 | Gehring et al. |
| 2004/0184459 A1 | * | 9/2004 | Elzur ......................... 370/392 |
| 2005/0138191 A1 | * | 6/2005 | Seto et al. ................... 709/230 |
| 2005/0197864 A1 | * | 9/2005 | Koritzinsky et al. ............ 705/2 |
| 2006/0067333 A1 | * | 3/2006 | Sivakumar et al. ..... 370/395.52 |

FOREIGN PATENT DOCUMENTS

JP 11-284682 A 1/2000

OTHER PUBLICATIONS

Austrian Office Action Jun. 23, 2005.

\* cited by examiner

*Primary Examiner*—Warner Wong
(74) *Attorney, Agent, or Firm*—Harness, Dickey & Pierce, P.L.C.

(57) ABSTRACT

A method, an apparatus and a system are disclosed for the adaptive and dynamic improvement or even optimization of a transport protocol when transmitting digital image data from a source system to a target system via a network. The apparatus accesses a database and a mapping module in which assignments of image data specific parameters and transport protocol specific parameters are stored.

24 Claims, 2 Drawing Sheets

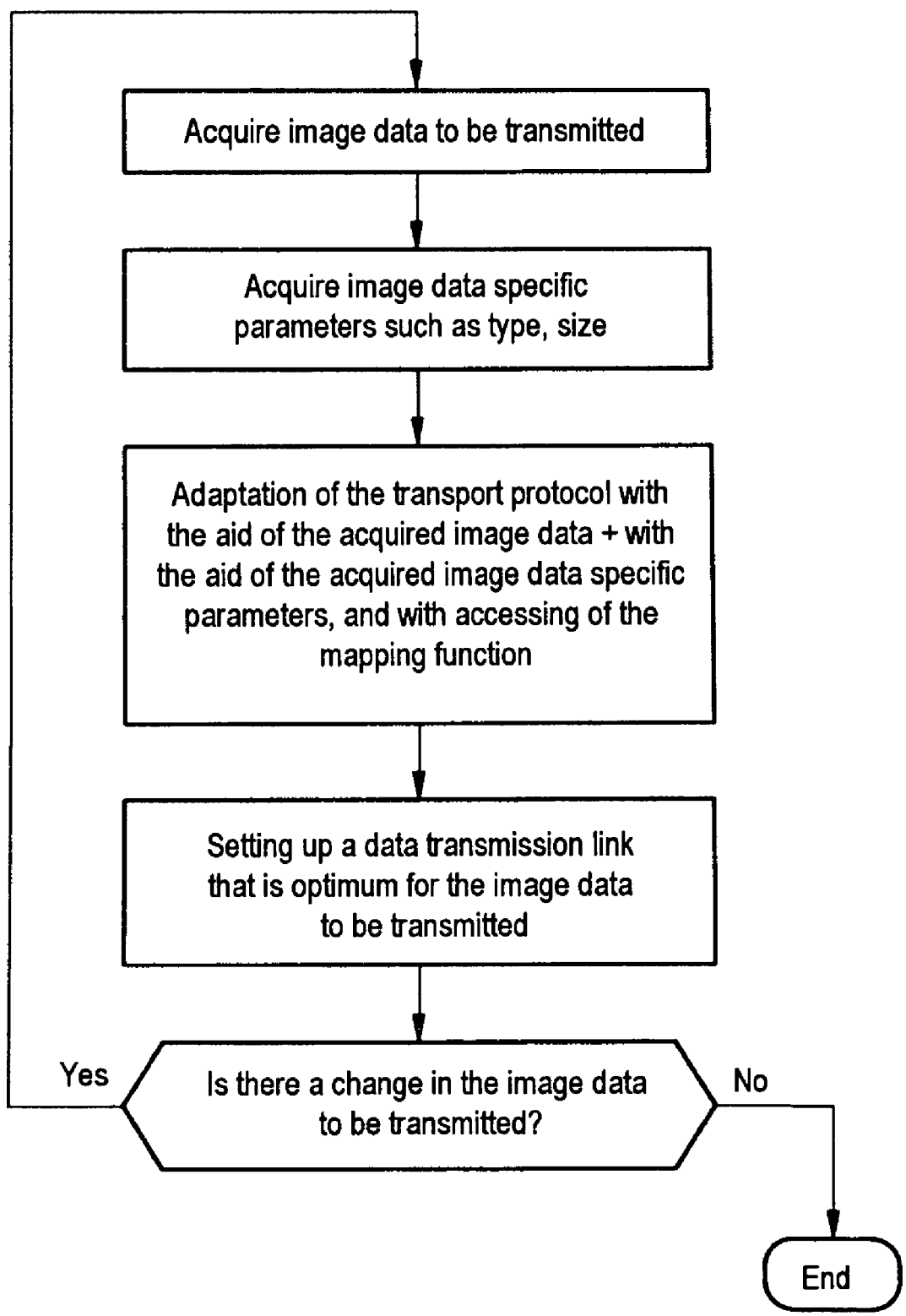

METHOD, APPARATUS AND SYSTEM FOR THE ADAPTIVE OPTIMIZATION OF TRANSPORT PROTOCOLS WHEN TRANSMITTING IMAGES

The present application hereby claims priority under 35 U.S.C. §119 on German patent application number DE 10 2004 036 488.5 filed Jul. 28, 2004, the entire contents of which is hereby incorporated herein by reference.

FIELD

The invention generally relates to a method for adapting transport protocols that are accessed via a network during transmission of data.

BACKGROUND

There are a number of standards in the medical field for communicating between the partially differing equipment. The DICOM standard is very frequently used, inter alia.

If image data are to be transmitted from the respective acquisition equipment such as, for example, an ultrasound unit or a magnetic resonance unit, to a workstation, a different type of data is involved than when, for example, so called reports, that is to say data from findings that are largely of a textual nature, are transmitted. Different demands are placed on the data transmission, depending on the type of data.

The fundamental transport protocol is responsible, in turn, for the type of data transmission. Thus, it can be expedient, for example, in some instances to admit large packets in the data transmission, while in other instances it turns out to be advantageous to stipulate only relatively small packets and, in turn, a higher frequency or a higher data transmission rate.

In most known medical applications, it has been customary to define as early as in the development phase which parameters are used for the configuration of the transport protocol. Consequently, the configuration of the transport protocol takes place as early as in an upstream phase and can be changed only with an increased outlay.

Consequently, it is no longer possible to react with unconstrained flexibility to different demands placed on the transport protocol. This procedure from the prior art therefore proves to be very disadvantageous.

Moreover, the transport protocol cannot be adjusted and/or adapted optimally to the current specific demands.

In order to avoid these disadvantages, systems have been developed that enable (renewed or adapted) configuration of the fundamental transport protocol even in a phase subsequent to the development phase. The disadvantage in these systems is, however, that there is always a need for a service technician to reconfigure the system on site. It has so far been impossible to adapt and optimize automatically.

SUMMARY

It is an object of an embodiment of the invention to indicate a way with the aid of which a transport protocol can be at least one of automatically, dynamically and adaptively improved or even optimized for transmitting data, in particular medical image data.

An object may be achieved by a method for automatically adapting at least one transport protocol that is designed for transmitting and/or receiving and for transmitting data from at least one source system to at least one target system, having the following:
automatically acquiring all the data specific parameters,
automatically accessing at least one mapping function that is designed to convert the acquired data specific parameters into transport protocol specific parameters, and
using the acquired parameters to adapt the transport protocol for the data to be transmitted.

Further achievements of the object may reside in an apparatus and/or a system for automatically adapting at least one transport protocol that is designed for transmitting data from at least one source system to at least one target system and that comprises the following:
an acquisition module intended for automatically acquiring all the data specific parameters,
a mapping module that is automatically accessed by the apparatus or the system and that comprises at least one mapping function that is designed to convert the acquired data specific parameters into transport protocol specific parameters, and
an adaptation module that is intended for adapting the transport protocol for the data to be transmitted with the aid of the acquired parameters.

An embodiment of the present invention is usually applied to digital image data, in particular from the medical field. There are different modalities here such as, for example, images of a computer tomograph, an ultrasound unit or other facilities. These acquired images have different properties. These properties are denoted below as data specific parameters and can, in particular, relate to the image size, image content or the type of compression method.

It is essential to an embodiment of the present invention that the transport protocol is adapted to a few parameters that are valid for the data currently to be transmitted. These parameters can relate exclusively only to the data to be transmitted, exclusively only to the fundamental network or to the transport protocol or else to a combination of these areas. The adaptation is therefore performed with the aid of the data specific, network specific and/or transport protocol specific parameters.

Depending on the application, the system administrator or user (in this case not identical to the end user) can determine which variables are to influence the configuration and/or adaptation of the transport protocol. For example, given very sharply varying loadings of the network it will be expedient to take account not only of the data specific parameters but also of network specific variables such as, for example, the current capacity utilization.

In an example embodiment of the invention, at least the source system and the target system are computer aided and belong to a network via which the transport is to be performed.

It is preferred that various transport protocols can be used and that the user can select one, normally when the system is firstly configured.

The parameters relating to the data to be transmitted are acquired by the source device or by an acquisition module. If the acquisition module is designed as a separate unit with reference to the source device, it can be provided that the acquisition module relays the acquired data to the source device. It is likewise possible for the acquisition module to be designed as an active unit that collects the data to be transmitted from the source device and also the associated metadata, that is to say the data specific parameters such as, for example, data type, data size, and then accesses the mapping function and optimizes the transport protocol adaptively.

The mapping function is an assignment function that on the one hand takes account of all the adjustable and/or configurable parameters of the transport protocol such as, for example, buffer sizes and packet sizes, and all the acquired parameters of the data to be transmitted such as, for example, image type and image size.

In an example embodiment, the mapping function accesses a database in which there are stored data records typically occurring for the respective source device—in a fashion referred to these data records—correspondingly configured or adjusted parameters of the transport protocol. It is thereby possible for the adaptation to be optimized, further automated and accelerated.

The method additionally may include the following step:
setting up a data transmission link with the aid of the acquired parameters and/or with the aid of the adapted transport protocol. That is to say, after the improved or even optimized configuration and adaptation of the transport protocol to the current data transmission, a data transmission link that corresponds to the acquired parameters can optionally be set up. This has the advantage that the planning optimization function is also converted for the current case.

It frequently occurs precisely in clinical use that changes also occur as data transmission is running, and these can also affect the data to be transmitted. Thus, for example, it is frequently the case that a physician requests an X-ray picture, for example, in order to compile his findings, and notices during the transmission or during the loading of the data that he is interested only in a small section of the image or of the series of images. The optimized design of the transport protocol is then performed in accordance with an embodiment of the invention firstly on the basis of the entire image.

After the change has been acquired, the method according to an embodiment of the invention is run through iteratively such that the inventive adaptation of the transport protocol is then performed on the basis of the image section. By repeatedly executing the method steps in conjunction with a change in the data or a change with regard to the network or the transport protocol, it is possible to ensure that the adaptation is performed dynamically such that the transport protocol is always adapted to the data currently to be transmitted.

The above-described, inventive embodiments of the method can also be designed as a computer program product having a computer-readable medium and having a computer program and associated program code segments, the computer being prompted after the computer program is loaded to carry out an embodiment of the above-described method according to an embodiment of the invention.

An alternative achievement of the object provides a storage medium that is intended for storing the abovedescribed, computer-implemented method and can be read by a computer.

BRIEF DESCRIPTION OF THE DRAWINGS

The following detailed description of the figures addresses example embodiments, which are not to be understood in a restricting way, together with their features and further advantages, this being done with the aid of the drawings, in which:

FIG. 2 shows a flowchart in accordance with an embodiment of the present invention.

DETAILED DESCRIPTION OF THE EXAMPLE EMBODIMENTS

Figure 1:
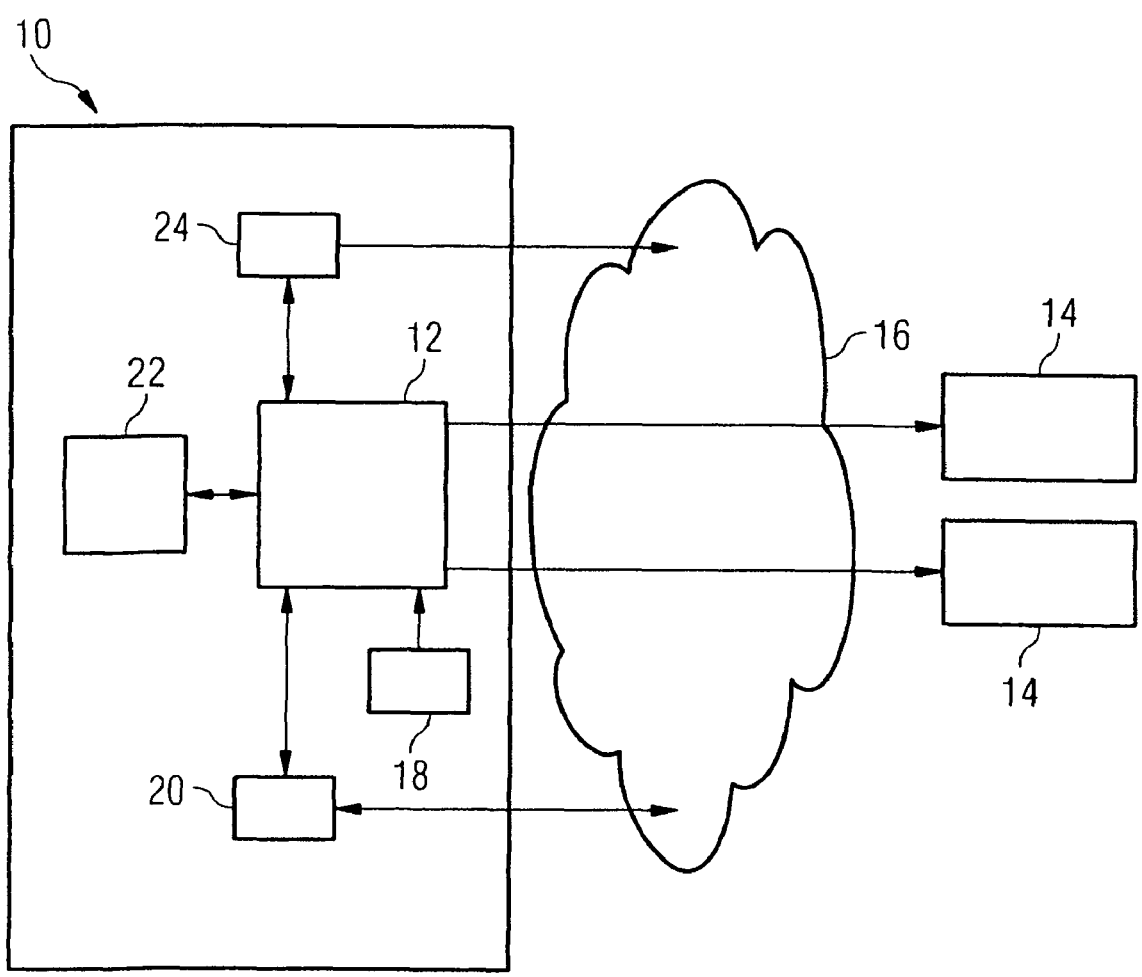
FIG. 1 shows a summary illustration of a number of elements in accordance with an embodiment of the present invention.

An apparatus denoted overall by 10 is designed for automatically and dynamically adapting a transport protocol. The aim is for data, in particular image data of medical content, to be transmitted from a source system 12 to a target system 14 via a network 16.

The apparatus 10 is designed according to an embodiment of the invention such that the transport protocol is automatically adapted optimally to the data to be transmitted.

The elements in accordance with an example embodiment of the invention are explained below with regard to FIG. 1. The apparatus further includes an acquisition module 20, a mapping module 22 and an adaptation module 24.

If the aim is, for example, to transmit digital medical images of an X-ray machine and a magnetic resonance machine from the respective source device 12 to the target device 14, a workstation of the investigating physician, these data are acquired in a first step according to an embodiment of the invention.

As shown in FIG. 2, the metadata belonging to these data such as image type, image size etc., are acquired in a subsequent step by accessing a database 18. The source system 12 itself preferably accesses the database 18. However, it is also possible to design the apparatus 10 such that the database is accessed by the mapping module 22 or some other module of the apparatus 10 that then relays the data thus acquired.

Consequently, both the image data that are actually to be transmitted, and the metadata relevant thereto are now available, specifically the data specific parameters such as image type (in the above example: X-ray images and magnetic resonance images) and image size etc.

Thereupon, the source system 12 or another module of the apparatus 10 can access the mapping module 22. There, the data specific parameters are converted into transport protocol specific parameters or assigned to the latter. This assignment is normally also performed once again by accessing the database 18, in which the most frequent or most common assignments are stored. That is to say, for example, it can be recorded that specific image types require a specific packet size for the transmission of the image data. Thus, in this step the transport protocol is adapted automatically to the data to be transmitted.

In an example development of an embodiment of the invention, it is provided to store templates, preferably in the database 18 or at another location. Diverse configuration scenarios are mapped in these templates. They include assignments that relate the data of the respective source system 12 to transport protocol specific data. That is to say it can be mapped in a template that, for example, the assumption is that, for example, an X-ray machine transmits only X-ray images and, since X-ray images require a likewise predefined configuration k of the transport protocol, the assignment of "X-ray machine—configuration k" is stored in the template.

The knowledge that leads to the storage of appropriate data in the database 18 can be extended by additional operating cycles. The method is thereby further automated. Thus, for example, it can be defined that specific sections always require a predefined configuration of the transport protocol.

In the next step, the acquired data and parameters are used to adapt the transport protocol automatically to the image data and/or image data series to be transmitted. The term transport protocol is intended here to be understood in the meaning of transport protocol process, since the transport protocol must run as a software process.

In an advantageous development, it is provided that the method additionally sets up a data transmission link in accordance with the adjustments generated. In this embodiment, the apparatus additionally further includes a connection module that is designed to set up an adapted data transmission link.

As soon as any changes now arise, should these affect the data to be transmitted or changes with regard to the transport protocol or with regard to the network 16, the method just described is then run through again such that it can be ensured that the adaptation according to the invention is always updated and reacts dynamically to changes. Costs can therefore be distinctly lowered by optimum design of the data transmission at any instant.

An embodiment of the present invention is normally designed to the DICOM standard which, for its part, is based on the TCP/IP protocol. The TCP/IP protocol recognizes the packet size and the buffer size, for example, as transport protocol specific parameters.

However, an embodiment of the method is not restricted to this standard, but can also be applied to other data types. For example, an embodiment of the method may be applied to other data types that are of a more textual nature, are predominant in the administrative sphere and/or are based on another protocol such as, for example, HL7.

The source system 12 is normally a source device, and the target system 14 is likewise a target device or a workstation. The terms are to be used synonymously in each case in the above description.

Any of the aforementioned methods may be embodied in the form of a system or device, including, but not limited to, any of the structure for performing the methodology illustrated in the drawings.

Further, any of the aforementioned methods may be embodied in the form of a program. The program may be stored on a computer readable media and is adapted to perform any one of the aforementioned methods when run on a computer device (a device including a processor). Thus, the storage medium or computer readable medium, is adapted to store information and is adapted to interact with a data processing facility or computer device to perform the method of any of the above mentioned embodiments.

The storage medium may be a built-in medium installed inside a computer device main body or a removable medium arranged so that it can be separated from the computer device main body. Examples of the built-in medium include, but are not limited to, rewriteable non-volatile memories, such as ROMs and flash memories, and hard disks. Examples of the removable medium include, but are not limited to, optical storage media such as CD-ROMs and DVDS; magneto-optical storage media, such as MOs; magnetism storage media, such as floppy disks (trademark), cassette tapes, and removable hard disks; media with a built-in rewriteable non-volatile memory, such as memory cards; and media with a built-in ROM, such as ROM cassettes.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

The invention claimed is:

1. A method for automatically adapting at least one transport protocol designed for transmitting data from at least one source system to at least one target system, comprising:
   automatically acquiring data specific parameters, the data-specific parameters are acquired from a group including medical image data type, medical image data size, medical image data content and type of compression of medical image data;
   automatically accessing at least one mapping function utilizing configuration templates, the at least one mapping function designed to convert the acquired data specific parameters into transport protocol specific parameters; and
   using the acquired parameters to adapt the transport protocol for the data to be transmitted, wherein the acquiring, accessing and using are applied iteratively as soon as a change occurs in the data to be transmitted, such that the transport protocol is always adapted to the data currently to be transmitted.

2. The method as claimed in claim 1, wherein the adaptation is performed using at least one of the data specific, network specific and transport protocol specific parameters.

3. The method as claimed in claim 1, wherein the adaptation is performed automatically.

4. The method as claimed in claim 1, wherein the transport protocol can be selected from a set of transport protocols.

5. The method as claimed in claim 1, wherein at least one source system and at least one target system are computer aided and belong to a network via which the transmission is to be performed.

6. The method as claimed in claim 1, wherein the parameters are acquired by at least one of the source system and an acquisition module that relays the acquired data to the source system.

7. The method as claimed in claim 1, wherein the mapping function takes account of at least one of all the adjustable and configurable transport protocol specific parameters and of all the acquired data specific parameters that are relevant for adapting the transport protocol.

8. The method as claimed in claim 1, wherein a database is accessed in which assignments of data specific parameters and transport protocol specific parameters are stored.

9. The method as claimed in claim 1, further comprising:
   setting up a data transmission link with at least one of the aid of the acquired parameters and use of the adapted transport protocol.

10. The method as claimed in claim 1, wherein the data are digital image data.

11. An apparatus for automatically adapting at least one transport protocol designed for transmitting data from at least one source system to at least one target system, the apparatus comprising:
    an acquisition module, configured to automatically acquire data specific parameters, the data-specific parameters are acquired from a group including medical image data type, medical image data size, medical image data content and type of compression of medical image data;
    a mapping module configured to utilize configuration templates, the mapping module automatically accessed by the apparatus and including at least one mapping function designed to convert the acquired data specific parameters into transport protocol specific parameters; and
    an adaptation module, configured to adapt the transport protocol for the data to be transmitted using the acquired parameters, wherein the apparatus is accessed iteratively as soon as at least one of the acquisition module and the apparatus indicates a change to the data to be transmitted such that the transport protocol is always adapted to the data currently to be transmitted.

12. The apparatus as claimed in claim 11, wherein the adaptation module is configured to adapt the transport protocol using at least one of the data specific, network specific and transport protocol specific parameters.

13. The apparatus as claimed in claim 11, wherein the adaptation is performed automatically.

14. The apparatus as claimed in claim 11, wherein the transport protocol is selectable from a set of transport protocols.

15. The apparatus as claimed in claim 11, wherein at least the source system and the target system are computer aided and belong to a network via which the transmission is to be performed.

16. The apparatus as claimed in claim 11, wherein the parameters are acquired by at least one of the source system and the acquisition module.

17. The apparatus as claimed in claim 11, wherein the mapping function of the mapping module takes account of at least one of all the adjustable and configurable transport protocol specific parameters and all the acquired data specific parameters that are relevant for adapting the transport protocol.

18. The apparatus as claimed in claim 11, wherein the apparatus accesses a database in which assignments of data specific parameters and transport protocol specific parameters are stored.

19. The apparatus as claimed in claim 11, further comprising:
a connection module, configured to set up a data transmission link using at least one of the acquired parameters and the adapted transport protocol.

20. The apparatus as claimed in claim 11, wherein the data are digital image data.

21. A system for automatically adapting at least one transport protocol that is designed for transmitting data from at least one source system to at least one target system, the system comprising:

an acquisition module, configured to automatically acquire data specific parameters, the data-specific parameters are acquired from a group including medical image data type, medical image data size, medical image data content and type of compression of medical image data;

a mapping module configured to utilize configuration templates, the mapping module automatically accessed by the system and including at least one mapping function designed to convert the acquired data specific parameters into transport protocol specific parameters; and an adaptation module, configured to adapting the transport protocol for the data to be transmitted with the aid of the acquired parameters, wherein the system is accessed iteratively as soon as at least one of the acquisition module and the apparatus indicates a change to the data to be transmitted such that the transport protocol is always adapted to the data currently to be transmitted.

22. The method as claimed in claim 1, wherein the data are digital image data from the medical field.

23. The apparatus as claimed in claim 11, wherein the mapping module accesses a database in which assignments of data specific parameters and transport protocol specific parameters are stored.

24. The apparatus as claimed in claim 11, wherein the data are digital image data from the medical field.

* * * * *